(12) United States Patent
Roesicke et al.

(10) Patent No.: US 8,577,437 B2
(45) Date of Patent: Nov. 5, 2013

(54) SYSTEM FOR IN-VIVO MEASUREMENT OF AN ANALYTE CONCENTRATION

(75) Inventors: Bernd Roesicke, Mannheim (DE); Juergen Rasch-Menges, Schwetzingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1532 days.

(21) Appl. No.: 12/052,313

(22) Filed: Mar. 20, 2008

(65) Prior Publication Data

US 2008/0234561 A1 Sep. 25, 2008

(30) Foreign Application Priority Data

Mar. 20, 2007 (EP) .................................. 07005637

(51) Int. Cl.
*A61B 5/00* (2006.01)
*A61B 5/05* (2006.01)

(52) U.S. Cl.
USPC ............................................ 600/345; 600/347

(58) Field of Classification Search
None
See application file for complete search history.

(56) References Cited

U.S. PATENT DOCUMENTS

| | | | |
|---|---|---|---|
| 5,497,772 A | 3/1996 | Schulman et al. | |
| 6,175,752 B1 * | 1/2001 | Say et al. | 600/345 |
| 6,584,335 B1 * | 6/2003 | Haar et al. | 600/322 |
| 6,809,653 B1 | 10/2004 | Mann et al. | |
| 6,835,553 B2 * | 12/2004 | Han et al. | 435/14 |
| 6,866,651 B2 | 3/2005 | Constantz | |
| 7,024,236 B2 * | 4/2006 | Ford et al. | 600/345 |
| 7,381,184 B2 * | 6/2008 | Funderburk et al. | 600/300 |
| 7,471,972 B2 * | 12/2008 | Rhodes et al. | 600/347 |
| 7,654,956 B2 * | 2/2010 | Brister et al. | 600/365 |
| 7,828,728 B2 * | 11/2010 | Boock et al. | 600/365 |
| 7,857,760 B2 * | 12/2010 | Brister et al. | 600/365 |
| 7,885,697 B2 * | 2/2011 | Brister et al. | 600/347 |
| 7,905,833 B2 * | 3/2011 | Brister et al. | 600/309 |
| 7,946,984 B2 * | 5/2011 | Brister et al. | 600/365 |
| 7,949,381 B2 * | 5/2011 | Brister et al. | 600/345 |
| 7,951,331 B2 * | 5/2011 | Roesicke et al. | 422/68.1 |
| 7,974,672 B2 * | 7/2011 | Shults et al. | 600/345 |
| 7,988,917 B2 * | 8/2011 | Roesicke et al. | 422/82.01 |
| 8,029,442 B2 * | 10/2011 | Funderburk et al. | 600/365 |
| 8,066,958 B2 * | 11/2011 | Rasch-Menges et al. | 422/430 |
| 8,075,496 B2 * | 12/2011 | Deck et al. | 600/583 |
| 8,083,928 B2 * | 12/2011 | Feldman et al. | 205/792 |
| 2002/0155425 A1 * | 10/2002 | Han et al. | 435/4 |
| 2003/0130597 A1 | 7/2003 | Marshall | |
| 2006/0016700 A1 * | 1/2006 | Brister et al. | 205/777.5 |
| 2006/0142651 A1 | 6/2006 | Brister et al. | |
| 2007/0191702 A1 * | 8/2007 | Yodfat et al. | 600/365 |
| 2008/0234561 A1 * | 9/2008 | Roesicke et al. | 600/345 |
| 2008/0242962 A1 * | 10/2008 | Roesicke et al. | 600/347 |
| 2009/0177062 A1 * | 7/2009 | Say et al. | 600/345 |
| 2009/0177065 A1 * | 7/2009 | Say et al. | 600/345 |
| 2009/0259118 A1 * | 10/2009 | Feldman et al. | 600/345 |
| 2010/0179404 A1 * | 7/2010 | Kamath et al. | 600/347 |
| 2010/0240974 A1 * | 9/2010 | Say et al. | 600/345 |
| 2010/0256471 A1 * | 10/2010 | Say et al. | 600/345 |
| 2011/0132778 A1 * | 6/2011 | Austera et al. | 205/792 |
| 2011/0230735 A1 * | 9/2011 | Wolfe et al. | 600/309 |
| 2011/0270055 A1 * | 11/2011 | Kraemer et al. | 600/309 |

FOREIGN PATENT DOCUMENTS

| | | | |
|---|---|---|---|
| EP | 1382363 A1 * | 7/2002 | |
| EP | 1266608 B1 * | 8/2006 | |
| EP | 1683484 B1 | 6/2007 | |

\* cited by examiner

Primary Examiner — Nita M Minnifield
(74) Attorney, Agent, or Firm — Harness, Dickey

(57) ABSTRACT

Human or animal body fluids can be measured in-vivo to determine analyte concentrations, such as glucose. The measurement system comprises an exchangeable sensor for in-vivo placement, a data carrier with calibration data for the sensor, a housing having a first chamber for receiving a sterile sensor and a second chamber for receiving a data carrier, and a base station that couples to the housing for transmitting measurement signals to an evaluation unit. Replacement sterile sensors can be packaged in a sterile package and the data carrier associated with the replacement sensor can be packaged in a non-sterile package.

21 Claims, 4 Drawing Sheets

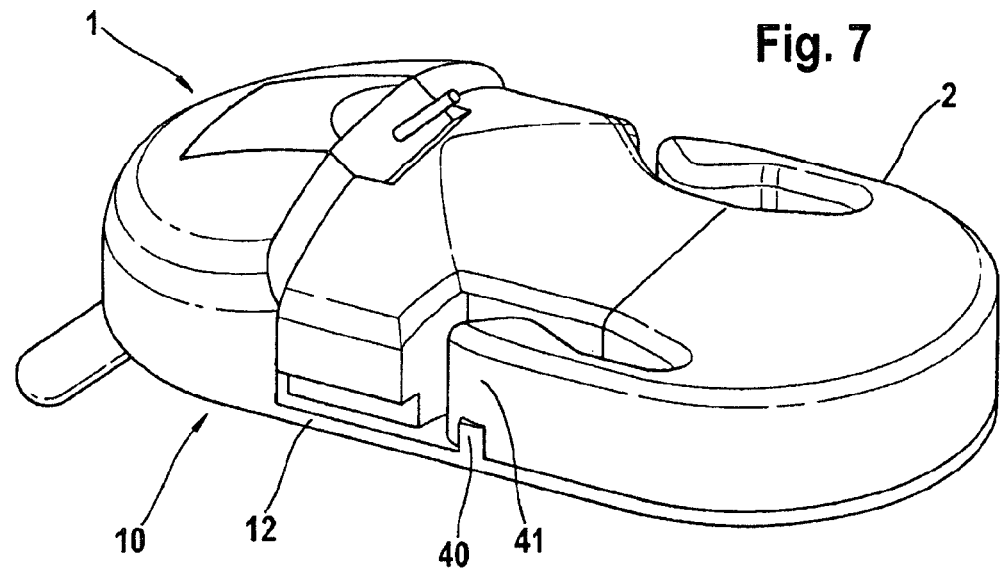
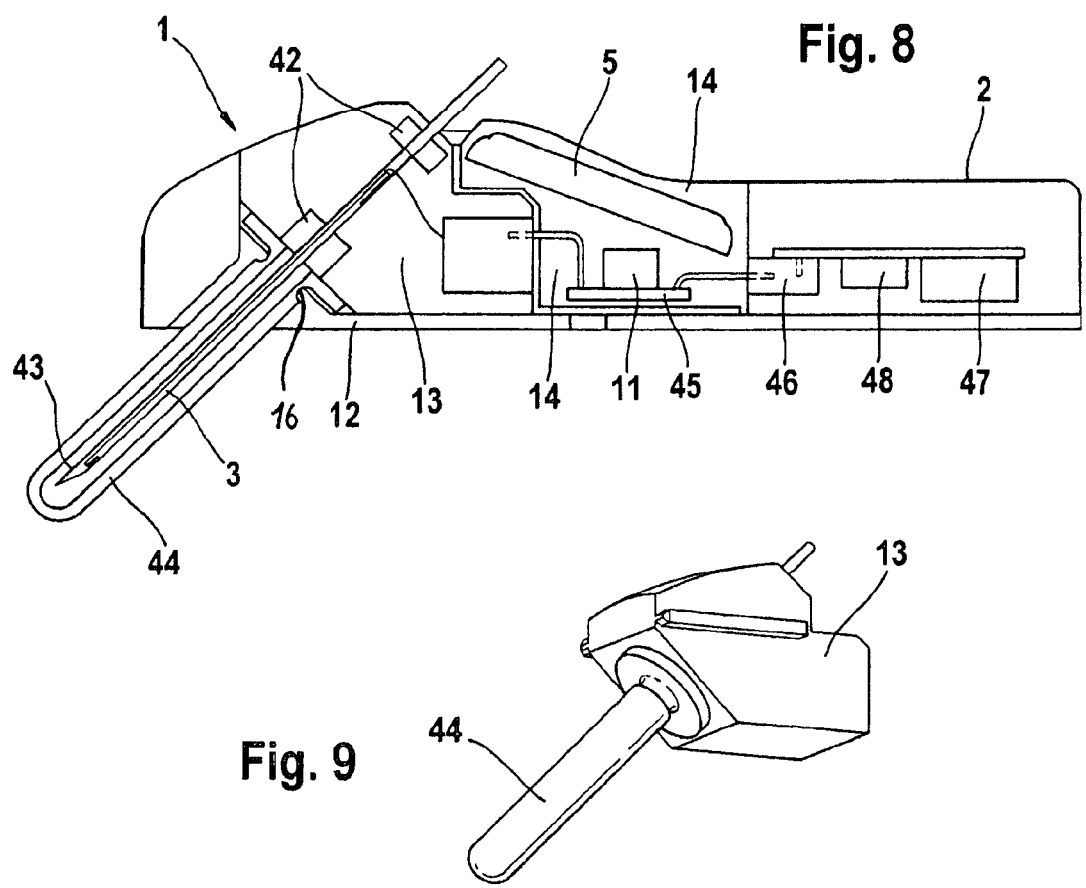

SYSTEM FOR IN-VIVO MEASUREMENT OF AN ANALYTE CONCENTRATION

REFERENCE

This application claims priority to European Patent Application No. EP 07005637.9 filed Mar. 20, 2007, which is hereby incorporated by reference.

FIELD

The disclosure relates to a system for the in-vivo measurement of an analyte concentration in a human or animal body.

BACKGROUND

As a general rule, sensors for the measuring of analyte concentrations of bodily fluids such as, e.g., blood or interstitial fluids cannot be manufactured with exactly preset measuring sensitivities. Typically, considerable deviations occur between production batches. To determine analyte concentrations by means of sensor signals provided by in-vivo measurements with sufficient exactitude for medicinal applications, calibration data are therefore required that were either determined at the pertinent sensor itself or by means of random testing of other sensors of the pertinent production batch. In general, such calibration data describe the difference between an ideal sensor sensitivity and a determined sensor sensitivity.

Systems for the in-vivo measurement of analyte concentrations typically comprise exchangeable sensors as exchange or consumable components and a long-life base station to which the exchangeable sensors are connected. This brings about the problem that at each exchange of sensor, new calibration data must be made available to the system.

Calibration data can be made available on a packing leaflet for the sensor and be manually entered by the user into the system. Because this procedure entails, however, the danger of input errors it is more beneficial to accompany each sensor or each sensor package with a data carrier with thereto stored calibration data in order to preclude the risk of input errors.

However, also this solution is not perfect since the risk exists that data carriers associated with different sensors could be transposed by the users and erroneous calibration data would thus be made available to a system which, in turn, would cause erroneous measuring results.

The sensors of an in-vivo measuring system must be sterile because they are inserted into the body of a patient. When being packaged together with a data carrier in a single housing, the customary method of sterilization, to wit, an intensive irradiation, entails considerable difficulties. Because electronic or magnetic data carriers are impaired due to the required radiation dose required for sterilization, it is not possible, or only with very expensive, especially manufactured data carriers, to irradiate the sealed housing with the therein arranged sensor and data carrier to sterilize the sensor.

SUMMARY

The in-vivo measurement of an analyte concentration in a human or animal body, comprising exchangeable sensors for generating measuring signals that correlate to the analyte concentration to be measured, data carriers with calibration data of the sensors, a base station to which at least one of the exchangeable sensors and a therewith associated data carrier with calibration data can be connected so that, during operation, measuring signals generated by a connected sensor can be transmitted to an evaluation unit that evaluates the measuring signals generated by the connected sensor by means of the calibration data that were read from the data carrier associated with the connected sensor. The invention relates further to a packaging system for exchange components of such a measuring system and a method for packaging of a sensor and a data carrier in which the sensor's calibration data are stored.

An embodiment of the housing is provided with at least two separate chambers wherein in a first chamber at least one of the sensors is arranged in sterile conditions and in the second chamber a data carrier with the calibration data of the sensor, wherein the housing is adapted to an interface of the base station so that the sensor in the housing and the therewith associated data carrier are connectable to the base station by setting the housing to the interface.

The sensor and the data carrier can be connected to the base station in a single operational step, insofar as the housing in which they are arranged is set to the base interface of the base station adapted to the housing. In such a manner, the risk of transposing data carriers or an erroneous connection of sensors can be effectively met.

The housing, wherein are arranged at least one sensor and a therewith associated data carrier, can be a packaging housing which is intended to be either totally or partially removed anew from the base station prior to effectuating an in-vivo measurement. However, it is also possible that while in operation, i.e., while performing in-vivo measurements, the housing continues to be connected to the base station.

The housing has at least two separate chambers. For the packaging of a sensor with a therewith associated data carrier the sensor is, at first, arranged in the first housing chamber, the housing is subsequently sealed and the sensor in the first housing chamber is sterilized by irradiation effect. After the completion of the sterilization process, the data carrier is arranged in the second housing chamber which is then closed. This method for the packaging of a sensor and a therewith associated data carrier is also an aspect of the invention.

A further aspect of the disclosure relates to a packaging system for exchange components of an in-vivo measuring system, according to the invention; the packaging system comprising a housing with at least two separate chambers, at least one sensor for generating measuring signals, that correlate to the analyte concentration to be measured, and a data carrier with calibration data of at least the one sensor, wherein the sensor is arranged under sterile conditions in a first chamber of the housing and the data carrier with the calibration data of the sensor is arranged in a second chamber of the housing.

BRIEF DESCRIPTION OF THE DRAWINGS

Further details and advantages of the invention are explained by means of embodiments with reference to the attached drawings.

FIG. 7 shows another embodiment of a system, according to the invention, for the in-vivo measurement of an analyte concentration in a human or animal body;

FIG. 8 shows a cross-sectional illustration of FIG. 7; and

FIG. 9 shows a sensor housing of the embodiment illustrated in FIGS. 7 and 8.

DETAILED DESCRIPTION

Figure 1:
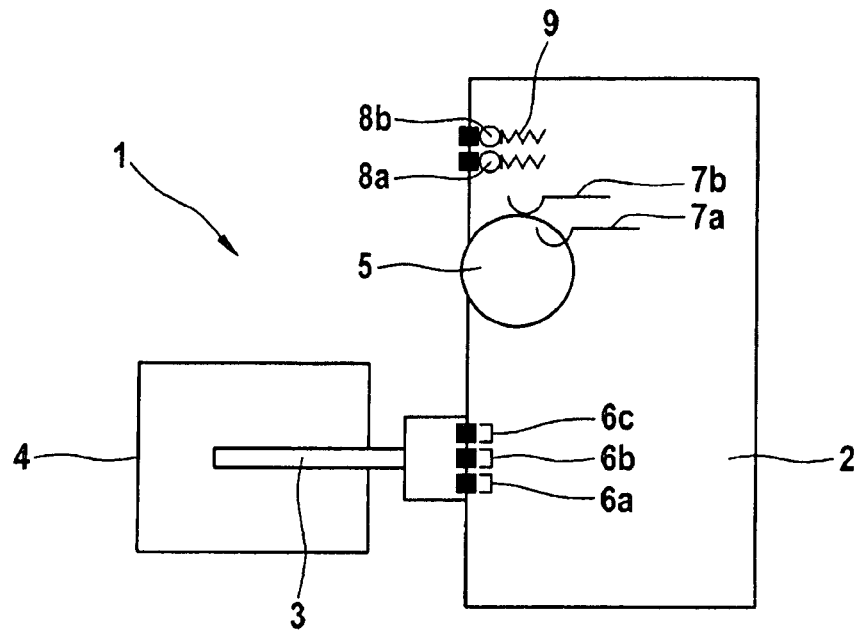
FIG. 1 shows a schematic representation embodiment of a base station and a thereto connected sensor of a system for the in-vivo measurement of an analyte concentration in a human or animal body.

FIG. 1 shows a schematic illustration of a base station 2 of a system 1 for the in-vivo measurement of an analyte concentration in a human or animal body with a sensor 3 connected to the base station 2 for generating measuring signals that correlate to the analyte concentration to be measured. FIG. 1 shows a human or animal body, symbolically represented by the box 4, into which is inserted the sensor 3 for an in-vivo measurement. In addition to the sensor 3, the system 1 comprises a battery 5 connected to the base station 2 as another consumable or exchange component.

The base station 2 is intended to be attached to the body of the patient during the in-vivo measurement and comprises a potentiostat that supplies the connected electro-chemical sensor 3 with electric current and holds a preset value of an electric potential at a measuring electrode of the sensor 3 with respect to the reference electrode of the sensor 3. The base station 2 also comprises an electronic evaluation unit which, during operation, evaluates by means of calibration data the measuring signals generated by a connected sensor 3. However, in principle it is also possible to arrange the evaluation unit in a device separate from the base station, to which device the measuring signals are made available by, e.g., radio or a data transfer line.

FIG. 1 shows connection contacts 6a, 6b, 6c of the base station 2 for connecting of the sensor 3, and connection contacts 7a, 7b of the base station 2 for connecting of the battery 5. The base station 2 has also at least one data input 8a, 8b for the connecting and the readout of a data carrier with calibration data, which can be removed from the base station 2 after the readout of the calibration data and which, therefore, is not shown in the operating state illustrated in FIG. 1. The data input 8a, 8b is coupled with spring elements 9 which, through elastic force, facilitate the attaching of a data carrier. The data carrier is preferably a storage chip so that the data input is formed by electric connection contacts. By way of example, the data carrier can also be a magnetic data carrier and the data input 8a, 8b can correspondingly comprise a reader head.

Figure 2:
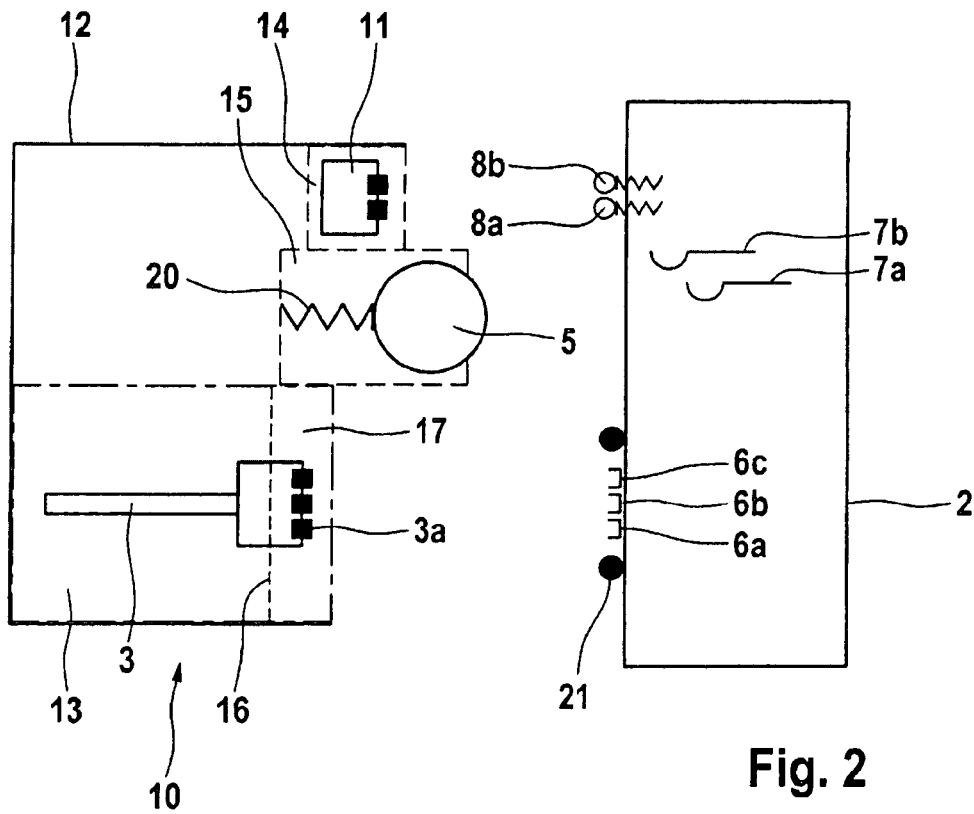
FIG. 2 shows the base station of the embodiment illustrated in FIG. 1 and an embodiment of a packaging system with exchange components to be connected to the base station.

FIG. 2 is a schematic illustration of the shown base station without connected exchange components. Additionally, FIG. 2 shows schematically a packaging system 10 for the exchange components (in particular, sensor 3, battery 5 and data carrier 11 with calibration data) which, together with the base station 2, constitute a system 1 for the in-vivo measurement of an analyte concentration in a human or animal body. The packaging system 10 comprises a housing 12 with at least two separate chambers 13, 14, 15, wherein in the first chamber 13 is arranged under sterile conditions the sensor 3 and in a second chamber the data carrier 11 with calibration data of the sensor 3. In the illustrated embodiment, the battery 5 is arranged in a third chamber 15.

Figure 3:
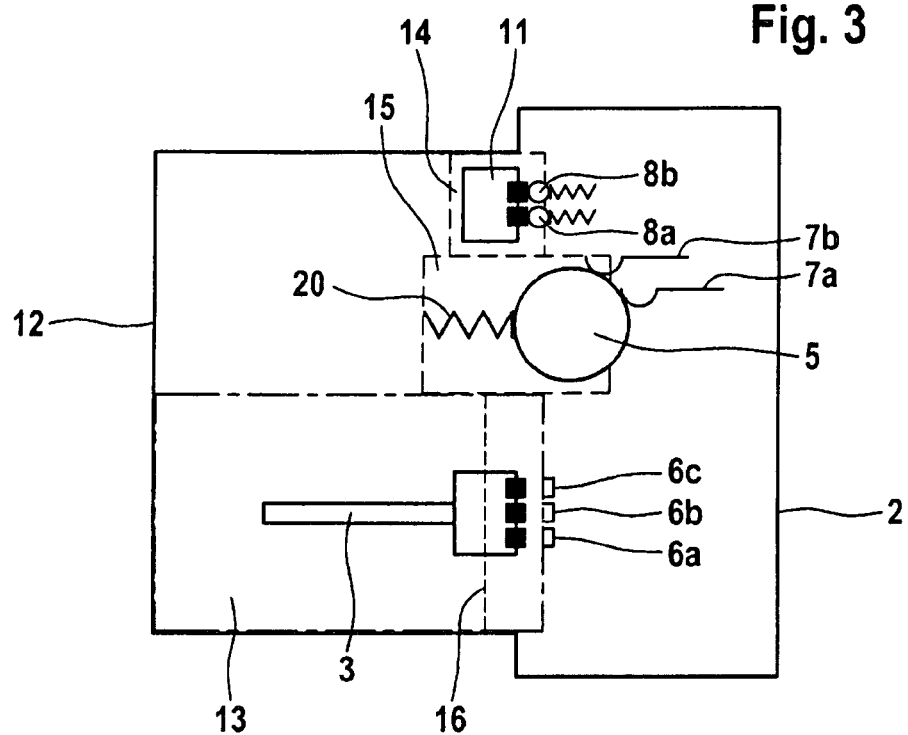
FIG. 3 shows a packaging system embodiment specified for the connection of the exchange components to the base station.

The housing 12 is fastened to an interface of the base station 2 in such manner that the sensor 3, arranged in the housing 12 and the therewith associated data carrier 11, can be connected to the base station by setting the housing 12 to the interface. FIG. 3 illustrates schematically the setting of the housing 12 to the interface of the base station 2 for the connecting of the exchange components 3, 5, 11. The measuring system 1 is automatically initialized by connecting the exchange components 3, 5, 11 and the measuring process is initiated.

For connecting the exchange components 3, 5, 11 arranged in the housing 12, the housing 12, in particular the sterile housing chamber 13, is opened. To facilitate the opening, the housing 12 of the illustrated embodiment is provided with a rupture joint 16 so that a user can easily break off a housing part 17, which seals the chambers 13, 14, 15, from the housing 12. This breakable housing part 17 can be configured, e.g., as a cap. In the herein illustrated embodiment, the housing part 17 seals both the sterile chamber 13 in which is housed the sensor 3 as well as the chambers 14, 15 wherein are arranged the data carrier 11 and the battery 5. It is, however, also possible to seal these chambers 13, 14, 15 by means of separate housing parts that must be removed separately. In particular, for the sealing of non-sterile chambers, e.g., the chambers 14, 15, housing the data carrier 7 or the battery 5, a removable sheeting or the like can also be used.

The housing 12 is provided with a spring element 20 that facilitates the connecting of the battery 5 when the housing 12 is set to the interface of the base station 2. Correspondingly, spring elements can also be arranged in the first chamber 13 and in the second chamber 14 to facilitate connecting of the sensor 3 and/or the data carrier 11 to the base station.

In the illustrated embodiment, the housing 12 and the interface of the base station 2 are adapted to each other in such a manner that, when the housing 12 is set to the interface, the battery 5 and the data carrier 11 are connected to the base station first and it is only afterwards that the sensor 3 is connected to the base station 2 by means of the thereto provided contacts 6a, 6b and 6c. In the illustrated embodiment, the sensor 3 has a flat structure and is connected to the base station 2 by means of a zero force plug 3a. The sensor 3 can also have, e.g., a sandwich structure or be configured rotationally symmetrical with the contacts 6a, 6b and 6c being adapted thereto.

A seal 21 of the base station 2, which in the illustrated embodiment is configured as a sealing ring, provides for a watertight coupling of the sensor 3 to the base station 2, so that no moisture can infiltrate into the inside of the base station 2. Thus, by way of example, the base station 2 can be placed on the abdomen of a patient without risk of being damaged by bodily fluids. The seal 21 effectuates a highly resistive sealing of the base station 2 and of the thereto connected sensor 3. In such a manner, the sensor 3 can be supplied with power as being an electro-chemical sensor by means of a potentiostat without being impaired by leakage currents.

Figure 4:
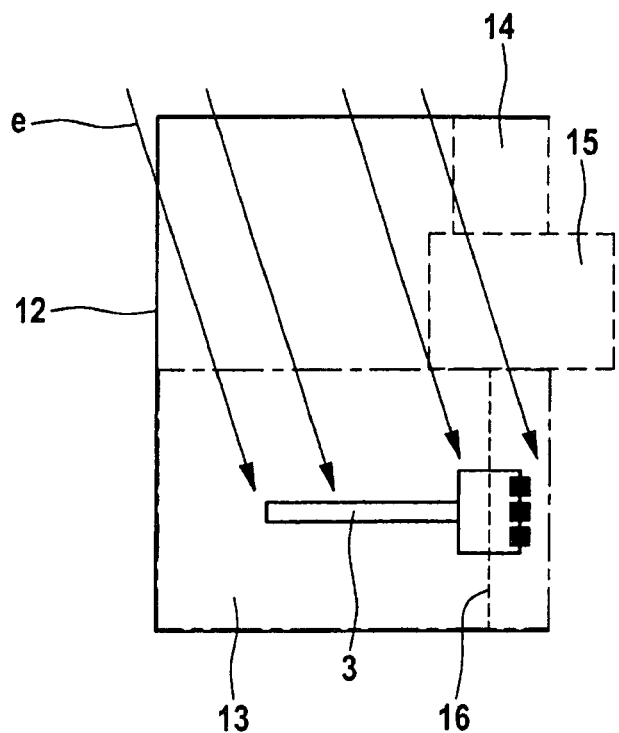
FIG. 4 shows an operational step for the manufacture of the packaging system illustrated in FIG. 2.

In the illustrated embodiment, the housing 12 is configured as a blister packaging. Compartments are formed in the plastic portion of the blister packaging that form the bottom and the walls of the chambers 13, 14, 15 of the housing 12. In a first operational step, illustrated in FIG. 4, a sensor 3 is arranged in the first housing chamber 13 whereupon the chamber 13 is sealed. Subsequently, the sensor 3 in the housing chamber 13 will be sterilized by irradiation. Especially appropriate are electron rays e with a dose of at last 20 kGy. In particular, especially appropriate is an electron ray dose of 28 kGy.

Figure 5:
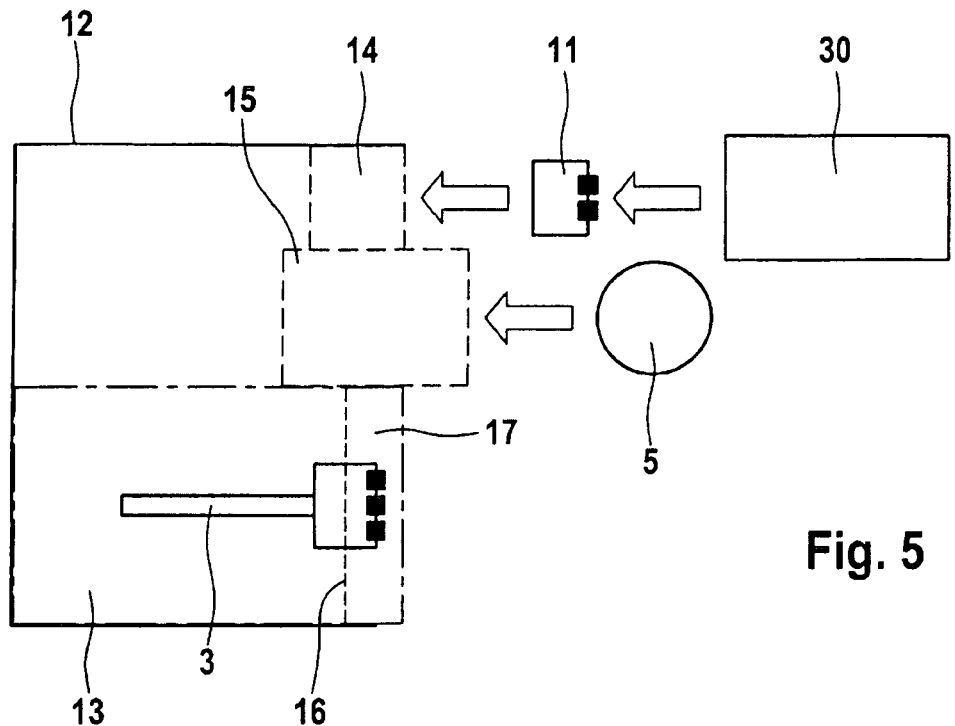
FIG. 5 shows another operational step for the manufacture of the packaging system.

In another operational step, illustrated in FIG. 5, the data carrier 11 is described with calibration data 30 of the sensor 3 arranged in the first housing chamber 13. These calibration data 30 are determined by means of random checks of the same production batch after conclusion of the sterilization process. Thereupon, the data carrier 11 is arranged in the second housing chamber 14 and the battery 5 in the housing chamber 15. Then the housing chamber 14, is sealed. The housing chambers 13, 14, 15 can be sealed in the customary manner in the blister packaging, e.g., by means of a plastic or metal sheeting.

Figure 6:
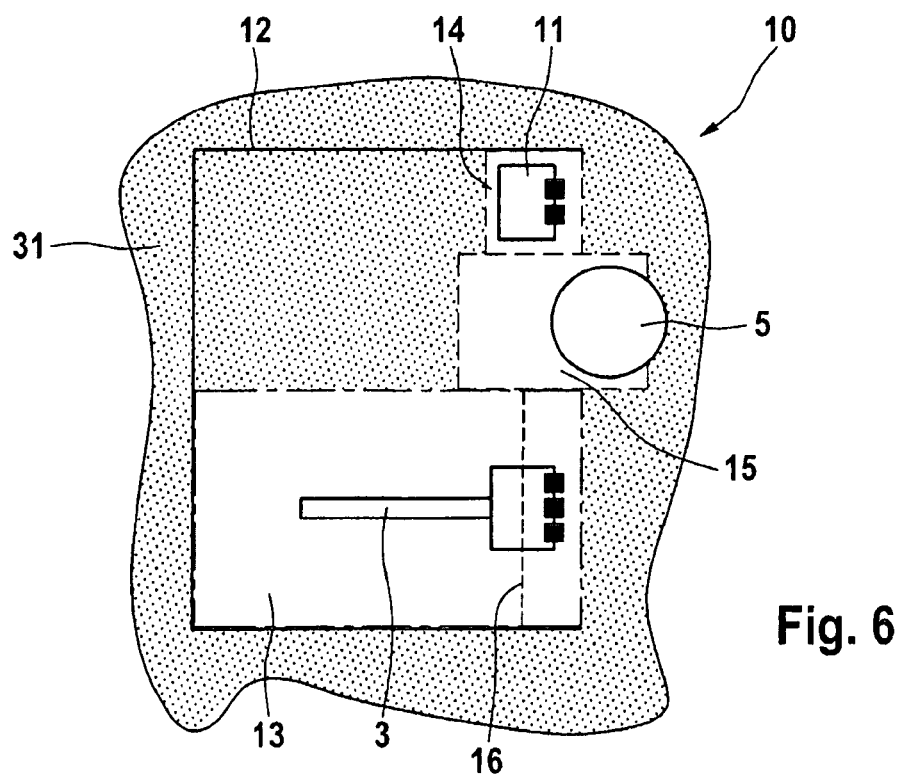
FIG. 6 shows the packaging system with an outer packaging.

In a last step, the completed packaging system 10 is packed in an outer packaging, in which it is sold, e.g., welded into a plastic sheet. FIG. 6 illustrates such a packaging system 10 with an outer packaging 31.

In the case of the embodiment explained above through FIGS. 1 to 6, the housing 12, containing the exchange components, is a packaging housing which is intended to be removed from the base station 2 prior to the carrying out of an in-vivo measurement. Hereinafter, by means of FIGS. 7 to 9 is explained another embodiment, wherein the housing 12, containing the exchange components, is fixed to the base station 2 during the carrying out of the in-vivo measurement.

FIG. 7 shows in a diagonal view the base station 2 with thereto attached housing 12 that contains the exchange components of system 1. FIG. 8 shows a cross-sectional view of FIG. 7 with the sterile housing chamber 13 with the therein arranged sensor 3 as well as the second housing chamber 14 with therein arranged battery 5 and data carrier 11 wherein are stored the calibration data of the sensor 3. The base station 2 is provided with a potentiostat 48 for the current and power supply of sensor 3 and an evaluation unit 47, configured as a microprocessor which, during operation, evaluates the measuring signals generated by the connected sensor 3 by means of the calibration data that were read from the data carrier 11 associated with the sensor 3. In principle, however, the potentiostat 48 can also be configured as a consumable component and arranged together with the sensor 3 in the housing 12, so that regarding high electrical resistance lower requirements can be placed on the sealing of the base. Furthermore, the evaluation unit 47 can be arranged in a device separate from the base station 2, which device can receive the data from the base station 2.

The housing 10 of the packaging system for consumable components is manufactured out of rigid plastic, alike to that of the base station 2. In the illustrated embodiment, the interface of the base station 2 and the housing 12 containing the consumable components are configured for an interlocking connection. The housing 12 is provided with drop-in lugs 40 that engage in thereto adapted recesses of the interface of the base station 2. These recesses are provided on the outsides of two spring legs 41 so that, by elastic force, the drop-in lugs are pressed into the recesses. The spring legs 41 can be compressed, so that the drop-in lugs 40 of the housing 12, containing the consumable components, are released from the thereto adapted recesses and the housing 12 can be removed from the base station 2. In a corresponding manner, with the spring legs 41 being compressed, the housing 12, containing the consumable components, can be fastened to the base station 2.

Alternatively or additionally to an interlocking connection, the housing containing the consumable components can be also configured in such a manner that, for the connecting of the sensor arranged in the housing, it can be fastened to the base station 2 by means of clamping.

The cross-section illustrated in FIG. 8 shows that the housing 12 is provided with two separate chambers 13, 14, wherein in a first chamber 13 the sensor 3 is arranged under sterile conditions and that, in the second chamber 14 are arranged a data carrier 11 with the calibration data of the sensor 3 and a battery 5 for the power supply of the base station 2. Connecting leads of the sensor 3 extend from the first chamber 13 into the second chamber 14 to a circuit board 45 that is connected to the data carrier 11 configured as a storage chip. The circuit board 45 is connected to the base station 2 by means of a plug connection 46, which in the illustrated embodiment is a multi-pole plug connection.

The sterile chamber 13, which contains the sensor 3, is sealed by two septa 42, whereby an insertion needle 43 for insertion of the sensor 3 into a human or animal body passes through the septa 42. The front end of the insertion needle 43 protruding from the chamber 13 is covered by a sterile protection cap 44 that is removed only when, by means of the insertion needle 43, the sensor 3 is to be inserted into the human or animal body. In the illustrated embodiment, the sterile protection cap 44 is fastened together with the rest of the housing 12 to a rupture joint 16.

To insert the sensor 3, the system 1, assembled from the packaging system and the base station, is placed, e.g., on the abdomen of a patient and the insertion needle 43 is stuck into the body of the patient. Subsequently, the insertion needle 43 that is configured, e.g., as a conduit carrying the sensor 3, can be withdrawn from the body of the patient while the sensor 3 remains inside the body of the patient.

For the packaging of the sensor 3 and a data carrier 11, in which are stored the calibration data of the sensor 3, the sensor 3 is first arranged in the first housing chamber 13 which is then sealed. For the manufacture of the embodiment illustrated in FIG. 8 in this operating step a sterile protection cap 44 is placed the end of the sensor 3 protruding from the first housing chamber 13 and the insertion needle 43 carrying the sensor 3, and the sterile protection cap 43 is connected to the housing chamber 13. Subsequently, the housing chamber 13 is subjected to an intensive electron radiation, so that the sensor 3 and the insertion needle 43 are be sterilized. FIG. 9 illustrates a detailed view of the first housing chamber 13 with the thereto affixed sterile protection cap 44 which, after the arranging of the sensor 3, are sterilized together by radiation.

In another operational step, the first housing chamber 13 is assembled with the second housing chamber 14 in order to create the housing 12 containing the consumable components and, thus, the above described packaging system 10 for the consumable components of the measuring system 1.

Thus, embodiments of the system for in-vivo measurement of an analyte concentration are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A system for the in-vivo measurement of an analyte concentration in a human or animal body, comprising:
    a sensor for the generating of measuring data that correlate to the analyte concentration to be measured;
    a data carrier with calibration data for the sensor;
    a base station configured for carrying the sensor and the data carrier; and,
    a housing adapted to an interface of the base station so that the sensor contained in the housing and the data carrier can be connected to the base station, the housing comprising a first chamber containing the sensor under sterile conditions and a second chamber containing the data carrier with the sensor's calibration data.

2. The system as in claim 1, further comprising an evaluation unit carried in the base station that evaluates measurement data according to the calibration data.

3. The system as in claim 1, further comprising a battery to supply power to the base station, the battery carried in the housing wherein the battery can be connected to the base station by interfacing the housing with the base station.

4. The system as in claim 1, further comprising a rupture joint contained in the housing for the removal of the housing part that seals the chamber containing the sensor.

5. The system as in claim 1 wherein the sensor is an electrochemical sensor configured for coupling to a potentiostat provided in the base station.

6. The system as in claim 1 wherein the housing is configured to be either totally or partially removed from the base station prior to the carrying out of an in-vivo measurement.

7. The system as in claim 1 wherein the housing or the base station are provided with a spring element that, upon setting the housing to the interface of the base station, facilitates connecting of the sensor or the data carrier to the base station.

8. A system for the in-vivo measurement of an analyte concentration in a human or animal body, comprising:
   a sensor as a consumable component for the generating of measuring data that correlate to the analyte concentration to be measured,
   a data carrier with calibration data of such a sensor,
   a base station to which the exchangeable sensor and the data carrier can be connected so that, while in operation, measuring signals generated by the sensor are transmitted to an evaluation unit that evaluates the measuring signals generated by the sensor by means of the calibration data,
   a means for housing the sensor under sterile conditions and the data carrier under non-sterile conditions wherein the housing is configured to couple to the base station.

9. The system as in claim 8 wherein the sensor is an electrochemical sensor configured for coupling to a potentiostat provided in the base station.

10. The system as in claim 8 wherein the evaluation unit is carried in the base station.

11. The system as in claim 8 wherein the housing is configured to be either totally or partially removed from the base station prior to the carrying out of an in-vivo measurement.

12. The system as in claim 8 wherein the housing or the base station are provided with a spring element that, upon setting the housing to the interface of the base station, facilitates connecting of the sensor or the data carrier to the base station.

13. A packaging system for the exchangeable components of an in-vivo measuring system, comprising:
   a housing having a first chamber configured for sterilization and a second chamber;
   a sensor carried in the first chamber, for the generating of measuring signals that correlate to an analyte concentration to be measured, the sensor being sterile; and,
   a data carrier carried in the second chamber, in which are stored the calibration data of the sensor,
   wherein, prior to effectuating an in-vivo measurement, the housing is configured to be totally or partially removed from a base station that connects with the sensor and the data carrier.

14. The packaging system as in claim 13 wherein the first chamber is configured for sterilization by irradiation.

15. The packaging system as in claim 13 wherein the sensor is an electro-chemical sensor configured for coupling to a potentiostat provided in the base station.

16. The packaging system as in claim 13, further comprising a rupture joint contained in the housing for the removal of the housing part that seals the chamber containing the sensor.

17. A method for the packaging of a sensor and data carrier in a housing for the in-vivo measurement of an analyte concentration, comprising:
   arranging a sensor in a first housing chamber of the housing;
   sealing the first housing chamber;
   sterilizing the sensor in the first housing chamber by means of irradiation;
   arranging a data carrier in a second housing chamber of the housing; and,
   closing the second housing chamber.

18. The method as in claim 17, further comprising providing a rupture joint contained in the first housing chamber, the rupture joint configured to expose the sensor upon rupturing.

19. The method as in claim 17 wherein the sensor is an electro-chemical sensor configured for coupling to a potentiostat provided in the base station.

20. The method as in claim 17, further comprising a battery carried in the second housing chamber.

21. The method as in claim 17, wherein the first housing chamber is adjacent to the second housing chamber.

* * * * *